US006638282B2

(12) United States Patent
Ramsey et al.

(10) Patent No.: US 6,638,282 B2
(45) Date of Patent: Oct. 28, 2003

(54) UMBILICAL CORD CUTTING AND CLAMPING DEVICE

(75) Inventors: James Ramsey, Coto de Caza, CA (US); Daniel R. Puchek, San Antonio, TX (US); David Cocke, San Antonio, TX (US); Bret Price, San Antonio, TX (US)

(73) Assignee: Cetus, LC, San Antonio, TX (US)

( * ) Notice: Subject to any disclaimer, the term of this patent is extended or adjusted under 35 U.S.C. 154(b) by 0 days.

(21) Appl. No.: 09/981,365

(22) Filed: Oct. 16, 2001

(65) Prior Publication Data

US 2003/0074009 A1 Apr. 17, 2003

(51) Int. Cl.[7] .............................................. A61B 17/12
(52) U.S. Cl. ....................................... 606/120; 606/157
(58) Field of Search ................................ 606/151, 153, 606/157, 158, 120

(56) References Cited

U.S. PATENT DOCUMENTS

| | | | | |
|---|---|---|---|---|
| 3,323,208 A | | 6/1967 | Hurley, Jr. ..................... 30/124 |
| 4,781,188 A | | 11/1988 | Collins ........................ 128/305 |
| 4,807,622 A | | 2/1989 | Ohkaka et al. .............. 128/305 |
| 4,856,517 A | | 8/1989 | Collins et al. ............... 128/346 |
| 4,938,215 A | * | 7/1990 | Schulman et al. ........... 606/120 |
| 5,462,555 A | * | 10/1995 | Bolanos et al. .............. 606/120 |
| 5,520,699 A | * | 5/1996 | Hessel et al. ................ 606/120 |
| 5,584,840 A | | 12/1996 | Ramsey et al. .............. 606/120 |
| 5,697,938 A | | 12/1997 | Jensen et al. ................ 606/120 |
| 5,913,862 A | | 6/1999 | Ramsey et al. .............. 606/120 |
| 6,205,680 B1 | * | 3/2001 | Clark ........................... 36/3 B |
| 6,341,376 B1 | * | 1/2002 | Smerdon, Jr. ..................... 2/16 |
| 2003/0004036 A1 | * | 1/2003 | Yoss ............................. 482/51 |

OTHER PUBLICATIONS

E–A–R Specialty Composites, http://www.earsc.com/CMS-Frame.asp?exturl=new/materials/confor.phtml&SID=5, Chart, Col. 5. Printed Mar. 7, 2003.*
E–A–R Speacialty Composites, http://www.earsc.com/applications.asp?id=133&childid=34&parentid=33, Paragraph 3, Printed Mar. 7, 2003.*
E–A–R Specialty Composites, http://www.earsc.com/applications.asp?id=140&childid=36&parentid=33, Paragraph 3, Printed Mar. 7, 2003.*

* cited by examiner

Primary Examiner—Michael J. Milano
Assistant Examiner—Bradford C Pantuck
(74) Attorney, Agent, or Firm—Gordon & Jacobson, P.C.

(57) ABSTRACT

A device includes first and second clamps each having an upper arm and a lower arm, and a cutting blade attached to one of the clamps. According to the invention, the upper arms of the first and second clamps are each provided with an upper clamping surface, and a directing member having a deformable cord gripping surface. The lower arms of the first and second clamps are each provided with a lower clamping surface, and a cord gripping surface. The clamping surfaces function to occlude the flow of blood through cut ends of the cord after the cord is cut by the blade, while the cord gripping surfaces function to prevent cord slippage prior to clamping by the clamping surfaces. Preferred gripping surfaces include deformable foam or resilient strips provided with teeth.

15 Claims, 4 Drawing Sheets

UMBILICAL CORD CUTTING AND CLAMPING DEVICE

BACKGROUND OF THE INVENTION

1. Field of the Invention

This invention relates broadly to umbilical cord clamps. More particularly, this invention relates to a device that simultaneously severs and clamps an umbilical cord.

2. State of the Art

The umbilical cord serves as the conduit between a mother and a fetus developing in the womb of the mother. Nutrients and oxygen within the blood of the mother pass through the umbilical cord to the fetus. Immediately after a baby is born, the umbilical cord must be clamped to stop the flow of blood therethrough and the cord must then be severed to separate the baby from the placenta. For many years, this procedure utilized two separate clamps to clamp the cord, and a scalpel to cut the cord between the clamps.

Over the past thirty years, a number of devices have been proposed for both clamping and cutting the cord in an abbreviated procedure, although few of them have been used commercially. For example, U.S. Pat. No. 3,323,208 to Hurley, Jr. shows an umbilical cord clamping device which includes two clamps held in side-by-side positioning by pins on one clamp which frictionally fit into holes on an abutting edge of the other clamp. A blade is positioned between the clamps and cuts the cord as the clamps are closed on the cord. However, the clamping jaws are the only mechanism securing the device to the cord, and are also the only mechanism restricting the blood flow pathway of the cord.

U.S. Pat. No. 4,807,622 to Ohkaka et al. shows a tube cutting and separating implement for severing a conduit (e.g. medical tubing). The patent discloses a grasping body having two sections integrally formed at a severable interior end and each section having an outside end which is flexible and curves and projects upward and inward toward the other outside end. Holding portions secure a tubing along a longitudinal axis of the grasping body. A blade is attached to one of the outside ends of the grasping body. When the outside ends of the grasping body are squeezed or otherwise directed toward the inside ends, flow restricting portions pinch off the tubing, and the blade first severs the tubing and then severs the interior ends of the integrally formed sections of the grasping body. A latching mechanism secures the ends of the grasping body. The device has a few drawbacks. First, the device does not adequately clamp the tubing to restrict fluid flow. Second, it requires enormous strength to puncture through both the tubing and the grasping body. Third, directing the blade through the grasping body in order to separate the sections further exposes the operator to injury due to potential contact with the blade.

U.S. Pat. No. 4,781,188 to Collins discloses an umbilical cord clamping and cutting device that includes two spaced apart clamps positioned within a clamping applicator. Closing the applicator simultaneously closes the two clamps. A blade is attached to one arm of the applicator, such that when the clamps are simultaneously closed on the cord, the blade automatically cuts the cord. The applicator is then opened and separated from the clamps which remain closed over the severed ends of the cord. The device requires an applicator and uses a relatively large number of parts.

U.S. Pat. No. 4,856,517 to Collins et al. discloses a similar device that includes two clamps positioned within an applicator. The clamps are locked in a closed position about an umbilical cord by a latch. A knob having a blade is fitted within a slot in the applicator and is manually moved forward to sever the cord with the blade. When the knob reaches the end of the slot, the latch is engaged and released by the knob to allow the opening and removal of the applicator, leaving the clamps fixed around the umbilical cord. The device requires two steps to operate; first, clamping the cord and, second, moving the blade. Furthermore, the device requires an applicator and has a relatively large number of parts, making manufacture of the device relatively expensive.

Each of the above patents pose serious drawbacks in their use and manufacture. First, as discussed above, many require the use of multiple steps, and/or are difficult to operate, and/or require the breaking frangible connections, and/or require the use of application devices. Second, the devices tend to have a large number of parts, making their manufacture expensive and complex. Third, the devices fail to securely grip the cord prior to cutting. Fourth, the devices further fail to securely hold the cut ends of the umbilical cord. As such, the cut ends of the umbilical cord may come loose or drip blood.

Co-owned U.S. Pat. Nos. 5,584,840 and 5,913,862 both to Ramsey et al. propose a solution to the shortcomings of previous devices. Both patents to Ramsey et al. disclose a device including two clamps friction fit in a side-by-side abutting relation, with a blade coupled between the clamps. Each clamp includes a molded outer guard. Using only two fingers, a practitioner may bring the arms of the clamps toward each other, such that the guards enclose and hold fast a section of umbilical cord, the blade projects into a space between the two clamps severing the cord, and interior serrated surfaces of the clamps provide clamping action. After the cord is clamped and severed, the two clamps may be easily separated using the same hand which operated to close the device, with one clamp remaining on the umbilical cord of the infant and the second clamp with blade attached being discarded along with the placenta. The Ramsey et al. devices are not only easy to operate, but are very easy and inexpensive to manufacture as they comprise only two molded clamps and an integrally positioned blade.

Though the devices of Ramsey et al. offer significant improvements over the prior art, clinical tests suggest that it is desirable to more effectively hold the umbilical cord prior to cutting and as well as to further limit potential blood splatter when cutting the cord.

SUMMARY OF THE INVENTION

It is therefore an object of the invention to provide an umbilical cord cutting and clamping device which is easy to operate and which cuts and clamps in a single motion.

It is another object of the invention to provide an umbilical cord cutting and clamping device which stably and securely holds the umbilical cord prior to complete cutting.

It is a further object of the invention to provide an umbilical cord cutting and clamping device which stably holds the cut ends of the umbilical cord.

It is an additional object of the invention is to provide an umbilical cord cutting and clamping device which reduces blood splatter.

It is yet another object of the invention to provide an umbilical cord cutting and clamping device which has absorbent surfaces.

It is yet a further object of the invention to provide an umbilical cord cutting and clamping device which is easy to manufacture.

In accord with these objects, which will be discussed in detail below, an umbilical cord cutting and clamping device includes first and second clamps each having an upper arm and a lower arm, and a cutting blade attached adjacent a medial side of one of the first and second clamps. According to the invention, the upper arms of the first and second clamps are each provided with an upper clamping surface, and a directing member having a deformable upper cord gripping surface. The lower arms of the first and second clamps are each provided with a lower clamping surface, and a lower cord gripping surface. The clamping surfaces function to occlude the flow of blood through cut ends of the cord after the cord is cut by the blade, while the cord gripping surfaces function to prevent cord slippage prior to clamping by the clamping surfaces.

According to one embodiment, the cord gripping surfaces include a compressible foam. According to another embodiment, the cord gripping surfaces of the upper arms include resilient strips provided with teeth, and the cord gripping surfaces of the lower arms includes mating teeth.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
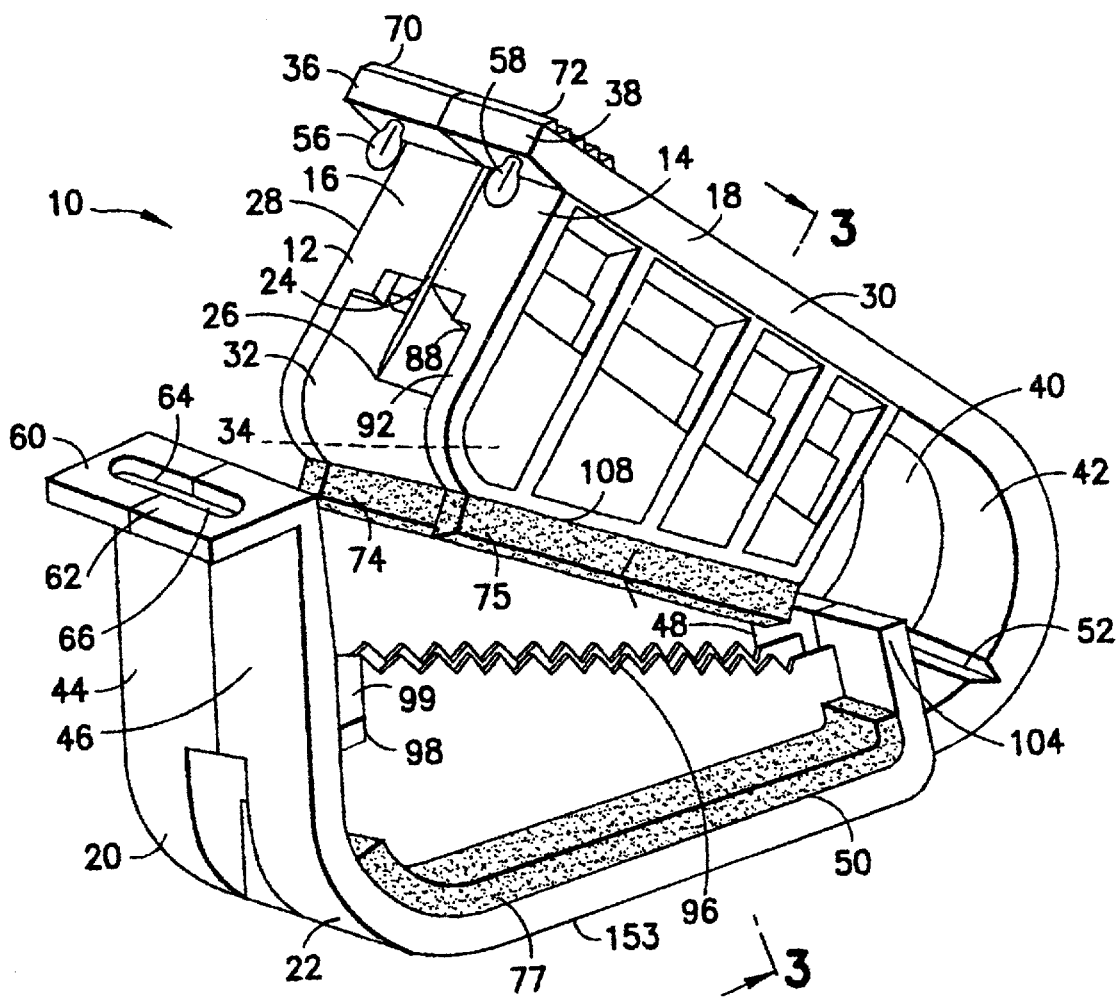
FIG. 1 is a perspective view of a first embodiment of a cord cutting and clamping device according to the invention.
Figure 2:
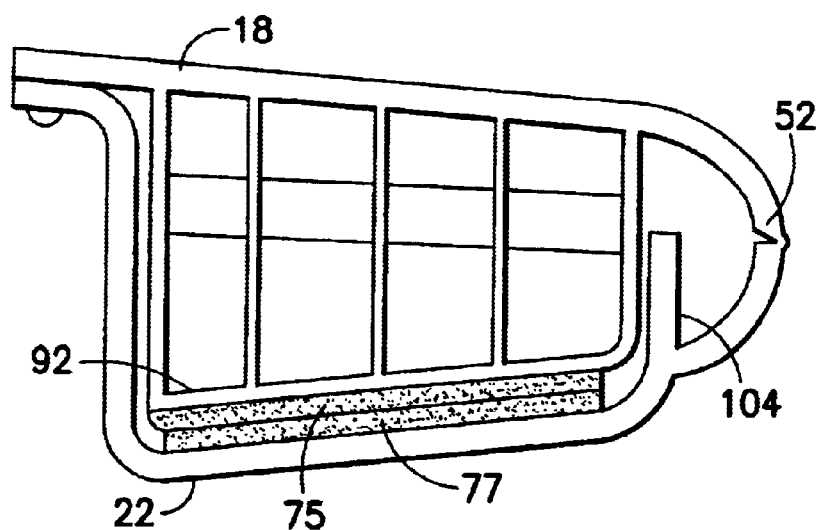
FIG. 2 is a perspective view of a first clamping member of the cord cutting and clamping device according to the invention in the closed position.

Turning now to FIGS. 1 and 2, a first embodiment of a cord cutting and clamping device 10 of the invention is shown. The cord cutting and clamping device 10 generally includes a first clamp 12 and a second clamp 14 coupled together by a friction fit, as described below. A blade 24 having a cutting edge 26 is coupled to the first clamp 12. Each of the clamps 12, 14 has an upper arm 16, 18 and a lower arm 20, 22, a lateral side 28, 30 and a medial side 32, 34, a distal end 36, 38 and a proximal end 40, 42, and an exterior surface 44, 46 and an interior surface 48, 50. The upper arms 16, 18 and the lower arms 20, 22 are joined at the proximal ends 40, 42 of the clamps 12, 14 by hinges 52 integrally formed with the arms 16, 18, 20, 22 which permits the upper arms 16, 18 to move relative to the lower arms 20, 22.

Knobs 56, 58 provided on the interior surfaces 48, 50 of the upper arms 16, 18 adjacent the distal ends 36, 38 of the clamps 12, 14 correspond to slots 64, 66 defined in tabs 60, 62 provided on the lower arms 20, 22 adjacent the distal ends 36, 38 of the clamps 12, 14. The slots 64, 66 are medially directed and adapted to receive and engage the knobs 56, 58 in a snap fit manner, thereby locking together the upper arms 16, 18 and lower arms 20, 22 adjacent the distal ends 36, 38 of the clamps 12, 14. When the knobs 56, 58 are engaged within slots 64, 66 of tabs 60, 62, the clamps 12, 14 are in a closed position. The exterior surface of the distal ends 36, 38 of the clamps 12, 14 adjacent the upper arms 16, 18 are preferably provided with a plurality of ridges 70, 72 which act as a gripping surface to help secure the device 10 within a hand of a user when operating the device 10. Further, the distal ends 36, 38 of the clamps 12, 14 adjacent the lower arms 20, 22 are preferably rounded to form a more comfortable shape for gripping and operating the device 10 within one hand.

Figure 3:
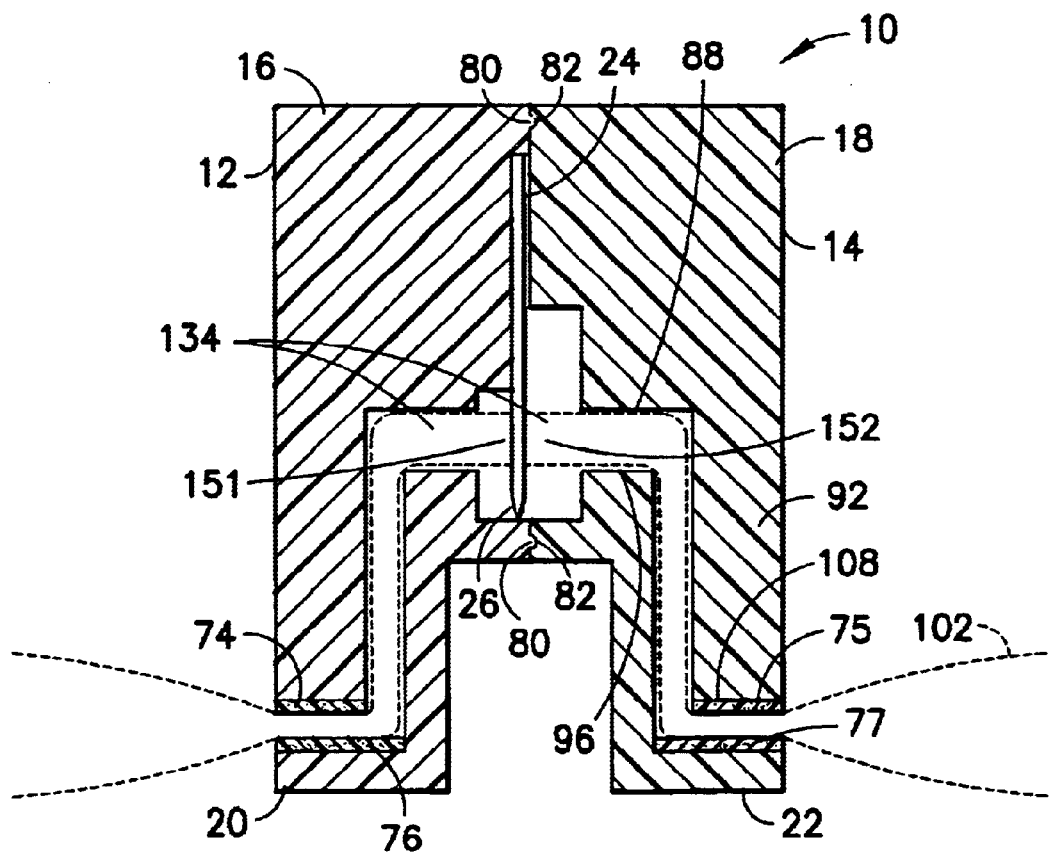
FIG. 3 is a cross-sectional view of the cord cutting and clamping device taken along line 3—3 in FIG. 1 when the device is in a closed-position about an umbilical cord.

Referring to FIG. 3, male fittings 80 provided on the medial side 34 of the second clamp 14 frictionally fit within female receptacles 82 defined in the medial side 32 of the first clamp 12 and are used to detachably couple the first clamp 12 to the second clamp 14 in a side-by-side abutting relation. The frictional engagement of the fittings 80 and receptacles 82 further provide for simultaneous movement of both upper arms 16, 18 relative to the lower arms 20, 22.

For the purpose of clarity, the second clamp 14 will now be described in detail with the understanding that the first clamp 12 is substantially a mirror image of the second clamp 14 and has associated elements with the same reference numerals with the exception of differences noted above. Referring to FIG. 1, the interior 50 of the upper arm 18 of the clamp 14 is provided with an upper clamping surface 88 positioned toward the medial side 34, and a cord directing member 92 positioned adjacent the lateral side 30 of the clamp 14. The lower arm 22 of the clamp 14 is provided with a lower clamping surface 96 positioned toward the medial side 34. The lower clamping surface 96 is preferably narrower than the upper clamping surface 88. The lower clamping surface 96 is preferably disposed at an angle relative to the bottom edge 153 of the lower arm 22 such that the lower clamping surface 96 slopes downward from the distal end 38 toward the proximal end 42 of the clamp 14. A hinge guard 104 is provided at a proximal end of the lower clamping surface 96 to prevent an umbilical cord from migrating proximally into the hinge 54 as the upper and lower clamping surfaces 88, 96 close about the cord 102. A guide 98 having an sloped surface 99 is provided on the lateral side of the distal end of the lower clamping surface 96. The guide 99 guides the cord directing member 92 into proper alignment as the clamp 14 is moved toward the closed position. When the clamp 14 is in the closed position, the upper clamping surface 88 and the lower clamping surface 96 are substantially parallel and preferably align medially in a proximal and distal direction. The upper clamping surface 88 is preferably between 0.2 and 0.3 inch wide, and the lower clamping surface 96 is preferably between 0.05 and 0.15 inch wide. The upper and lower clamping surfaces 88, 96 are preferably between 1.5 and 2.0 inches long, and are preferably serrated or ribbed to provide a gripping surface to help prevent a cord 102 from slipping between the clamping surfaces 88, 96 as the upper arm 18 is brought toward the lower arm 22.

The cord directing member 92 of the upper arm 18 has a bottom 108 which is angled relative to the exterior surface 46 of the upper arm 18 of the clamp 14 and which projects substantially ahead of the cutting edge 26 of the blade 24. The angled bottom 108 provides a more even distribution of downward pressure along the cord 102 as the upper and lower arms 18, 22 are rotated together. That is, when the cord directing member 92 is rotated toward the lower clamping surface 96, the cord directing member 92 becomes substantially parallel with the lower clamping surface 96 when aligned therewith and finally becomes parallel with the bottom edge 153 of the lower arm 22 when the clamp is closed.

According to the invention, the upper arms 16, 18 are provided with an upper cord gripping surface 74, 75, and the lower arms are provided a lower cord gripping surface 76, 77. According to the first embodiment of the invention, the gripping surfaces are a preferably deformable foam. Preferred foams are those having a nominal density of approximately 5.8 pcf, and a compression set of approximately 0.6 percent when compressed twenty five percent and approximately 2.4 percent when compressed fifty percent. A preferred foam is the CONFOR® CF-40 urethane foam sold by the E-A-R Specialty Composites business unit of Aearo Company of Indianapolis, Ind. Other foams of other densities and compression sets may also be used. The upper and lower cord gripping surfaces are adapted to contour to a cross-sectional shape of an umbilical cord 102 and grip the cord to prevent cord slippage prior to complete clamping by the clamping surfaces. Furthermore, the cord gripping surfaces allow the clamp to accommodate cords of various diameters and consistencies. Moreover, the foam provides absorbency to retain blood which may drip from the cut ends of the umbilical cord 102.

Referring now to FIG. 3, when the clamping device is provided about an umbilical cord, and the clamps 12, 14 close about the cord 102, the cord gripping surfaces 75, 76 of the cord directing members 92 contact the cord 102 and force a first portion 134 of the cord against the lower clamping surfaces 96. As the upper arms 16, 18 are further moved toward the lower arms 20, 22, the cord gripping surfaces 75, 76, 77, 78 of the cord directing members 92 and lower arms 22 capture a second portion of the cord and securably hold the cord within the clamp to substantially prevent any migration. The blade 24 is then adapted to sever the first portion 134 of the cord 102 between the clamps 12, 14 as the clamps are closed about the cord 102. When the clamps 12, 14 are completely closed about the cord 102 (i.e., the knobs 56, 58 are locked in the slots 64, 66), the severed ends 151, 152 of cord 102 are clamped and secured between the upper clamping surfaces 88 and the lower clamping surfaces 96. The two clamps 12, 14, which are each securing one of the severed ends 151, 152 of the cord 102 may thereafter be separated without loss of fluid from the cord 102 by simply releasing the male and female friction fit couplings 80, 82 and moving the first clamp 12 away from the second clamp 14.

The device 10 is preferably formed from a rigid plastic such as polypropylene, polyethylene, or nylon; and is preferably designed having thin walls 158 supported by vertical supports 160 so that the device 10 is lightweight yet strong, and uses less plastic thereby reducing costs to manufacture, reducing time to cure the plastic, reducing weight of the clamps, and simultaneously reducing waste which must eventually be disposed.

Figure 4:
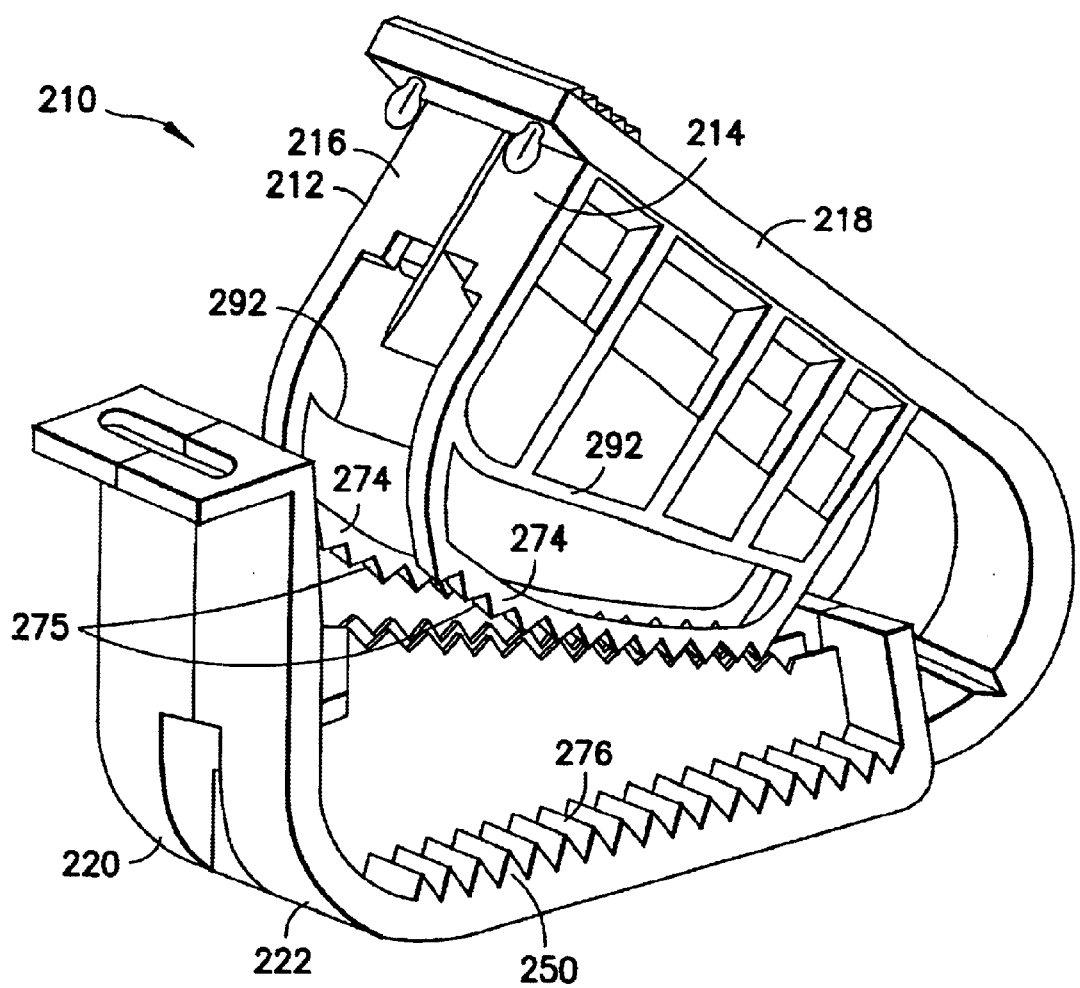
FIG. 4 is a perspective view of a second embodiment of a cord cutting and clamping device according to the invention.
Figure 5:
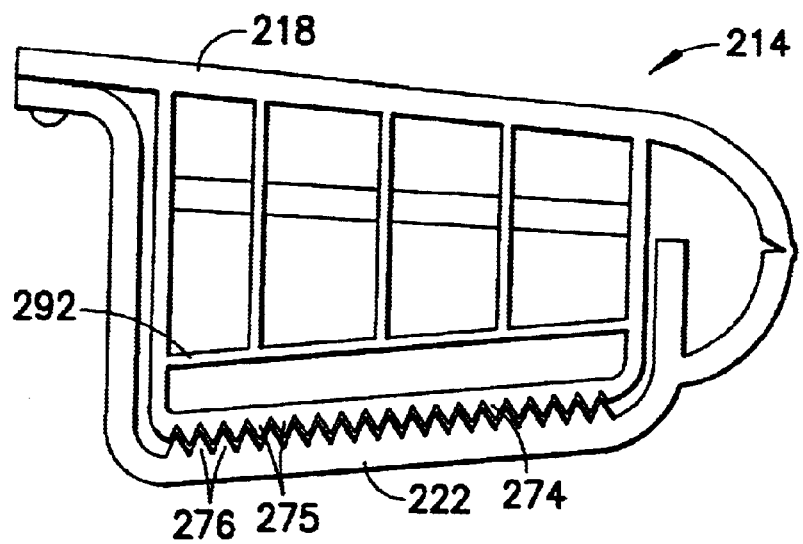
FIG. 5 is a side elevation of the second embodiment of the cutting and clamping device shown in a closed position, without an umbilical cord in the clamp.
Figure 6:
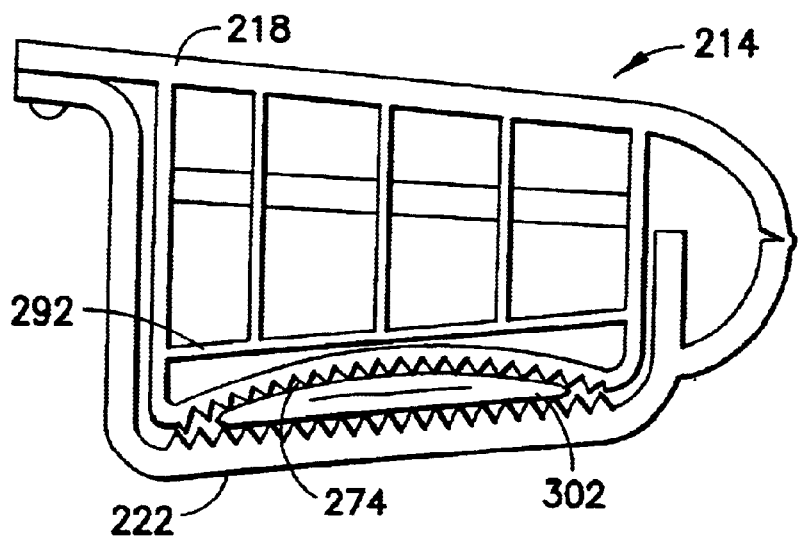
FIG. 6 is a side elevation of the second embodiment of the cutting and clamping device shown closed about an umbilical cord.

Turning now to FIGS. 4 and 5, a second embodiment of the clamping device 210, substantially similar to the first embodiment, is shown. The differences between the first and second embodiments is at the cord gripping surfaces adapted to hold the cord prior to complete clamping and cutting. The directing members 292 of the upper arms 216, 218 of the clamps 212, 214 include descending resilient strips 274 provided with cord engaging structure such as teeth 275. The interior surfaces 250 of the lower arms 220, 222 of the clamps are also provided with cord engaging structure such as teeth 276. The upper and lower teeth 275, 276 preferably, though not necessarily, mate (FIG. 5). As shown in FIG. 6, when the clamping device is provided about an umbilical cord 302, the resilient strip 274 "gives" to deform and then conform about the particular cord, while the teeth 275, 276 on the strip and the lower arm stably hold the cord during cord clamping and cutting.

There have been described and illustrated herein embodiments of a cord cutting and clamping device. While particular embodiments of the invention have been described, it is not intended that the invention be limited thereto, as it is intended that the invention be as broad in scope as the art will allow and that the specification be read likewise. Thus, while particular materials forming the device have been disclosed, it will be appreciated that other rigid materials may be used as well. Also, while a cord cutting and clamping device having a dual clamping system is preferred, it will be recognized that the device can be formed having only one clamp having a blade disposed thereon. In addition, while two examples of a cord gripping surfaces have been described, it will be appreciated that other such structure may be used. For example, spikes, adhesives, foam, flexible resilient tubing, rubber, etc. all may be used. Furthermore, the cord directing member and the lower arm each may have different cord gripping surfaces. Moreover, while in the second embodiment the upper arm has the resilient strip, it will be appreciated that, in addition or in the alternative, the lower arm may have a deformable resilient strip. In addition, while a cord directing member having an angled bottom was disclosed, it will be appreciated that the bottom need not be angled relative to the lower clamping surface; and while an angled lower clamping surface is preferred, it will be appreciated that the lower clamping surface need not be angled relative to the lower arm. While a knob and slot latching mechanisms has been disclosed, it will be understood that other latching mechanisms can be used instead. It will therefore be appreciated by those skilled in the art that yet other modifications could be made to the provided invention without deviating from its spirit and scope as claimed.

What is claimed is:

1. An umbilical cord cutting and clamping device, comprising:
   a) a first clamp having a first lower arm and a first upper arm movable relative to said first lower arm, each of said first upper arm and said first lower arm having a lateral side and a medial side,
      said first upper arm provided with a first substantially rigid upper clamping surface and a first directing member having a first deformable cord gripping surface, and
      said first lower arm provided with a first lower clamping surface;
   b) a second clamp having a second lower arm and a second upper arm movable relative to said second lower arm, each of said second upper arm and said second lower arm having a lateral side and a medial side,
      said second upper arm provided with a substantially rigid second upper clamping surface,
      said second lower arm provided with a substantially rigid second lower clamping surface;
   c) a retaining means for detachably coupling said first clamp to said second clamp and for maintaining said first clamp and said second clamp in a side-by-side abutting relation; and
   d) a blade coupled adjacent a medial side of one of said first upper arm of said first clamp and said second upper arm of said second clamp, said blade having a cutting edge extending below both said first upper clamping surface and said second upper clamping surface.

2. An umbilical cord cutting and clamping device according to claim 1, wherein:
   said first cord gripping surface is conformable to the umbilical cord.

3. An umbilical cord cutting and clamping device according to claim 1, wherein:
   said first lower arm of said first clamp has a second deformable gripping surface, and wherein when said first and second clamping surfaces are clamped about the umbilical cord, said first and second deformable cord gripping surfaces are deformed by the umbilical cord.

4. An umbilical cord cutting and clamping device according to claim 3, wherein:
   said first and second cord gripping surfaces are conformable to the umbilical cord.

5. An umbilical cord cutting and clamping device according to claim 3, wherein:
   said first and second deformable cord gripping surfaces comprise a foam.

6. An umbilical cord cutting and clamping device according to claim 5, wherein:
   said foam has a density of approximately 5.8 pcf.

7. An umbilical cord cutting and clamping device according to claim 1, wherein:
   said first deformable cord gripping surface is a resilient strip descending from said upper arm of said first clamp.

8. An umbilical cord cutting and clamping device according to claim 7, wherein:
   said resilient strip is provided with teeth.

9. An umbilical cord cutting and clamping device according to claim 8, wherein:
   said first lower arm of said first clamp is provided with teeth.

10. An umbilical cord cutting and clamping device according to claim 9, wherein:
    said teeth of said first lower arm are adapted to mate with said teeth of said resilient strip when said first clamp is closed.

11. An umbilical cord cutting and clamping device according to claim 1, wherein:
    said first clamp includes a first locking means for coupling a first end of said first upper arm to said first end of said first lower arm, and said second clamp includes a second locking means for coupling a first end of said second upper arm to said first end of said second lower arm.

12. An umbilical cord cutting and clamping device according to claim 1, further comprising:
    e) a first hinge for rotatably coupling said second end of said first upper arm of said first clamp to said second end of said first lower arm of said first clamp; and
    f) a second hinge for rotatably coupling said second end of said second upper arm of said second clamp to said second end of said second lower arm of said second clamp.

13. An umbilical cord cutting and clamping device according to claim 1, wherein:
    at least one of said first clamp and said second clamp is provided with a guide which aligns said respective upper clamping surface relative to said respective lower clamping surface.

14. An umbilical cord cutting and clamping device, comprising:
    a) a first clamp having a first lower arm and a first upper arm movable relative to said first lower arm,
       said first upper arm provided with a first substantially rigid upper clamping surface and said first lower arm provided with a first lower clamping surface,
       at least one of said first upper arm and said first lower arm being provided with a first absorbent material;
    b) a second clamp having a second lower arm and a second upper arm movable relative to said first lower arm,
       said second upper arm provided with a second substantially rigid upper clamping surface and said second lower arm provided with a second lower clamping surface,
       at least one of said second upper arm and said second lower arm being provided with a second absorbent material;
    c) a retaining means for detachably coupling said first clamp to said second clamp and for maintaining said first clamp and said second clamp in a side-by-side abutting relation; and
    d) a blade coupled adjacent a medial side of one of said first upper arm of said first clamp and said second upper arm of said second clamp, said blade having a cutting edge extending below both said first upper clamping surface and said second upper clamping surface.

15. An umbilical cord cutting and clamping device according to claim 14, wherein:
    said first and second absorbent materials are foam.

\* \* \* \* \*